United States Patent
Li (10) Patent No.: US 12,140,531 B2
(45) Date of Patent: Nov. 12, 2024

(54) DETECTION DEVICE AND DETECTION METHOD

(71) Applicants: BEIJING BOE HEALTH TECHNOLOGY CO., LTD., Beijing (CN); BOE TECHNOLOGY GROUP CO., LTD., Beijing (CN)

(72) Inventor: Hongquan Li, Beijing (CN)

(73) Assignees: BEIJING BOE HEALTH TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 482 days.

(21) Appl. No.: 17/417,423

(22) PCT Filed: Nov. 9, 2020

(86) PCT No.: PCT/CN2020/127470
§ 371 (c)(1),
(2) Date: Jun. 23, 2021

(87) PCT Pub. No.: WO2021/103992
PCT Pub. Date: Jun. 3, 2021

(65) Prior Publication Data
US 2022/0082494 A1    Mar. 17, 2022

(30) Foreign Application Priority Data
Nov. 29, 2019   (CN) .......................... 201911201283.5

(51) Int. Cl.
*G01N 21/31* (2006.01)
*B01L 3/00* (2006.01)
(Continued)

(52) U.S. Cl.
CPC ............ *G01N 21/31* (2013.01); *B01L 3/5027* (2013.01); *B01L 3/505* (2013.01); *G01N 21/01* (2013.01);
(Continued)

(58) Field of Classification Search
CPC ........ G01N 21/31; G01N 21/01; G01N 21/27; G01N 33/00; G01N 21/78;
(Continued)

(56) References Cited

U.S. PATENT DOCUMENTS 5,518,688 A  *  5/1996  Gianino .......... G01N 35/00029
                                                  422/561
2004/0156049 A1* 8/2004 Breninger .......... G03F 7/70933
                                                  356/364
(Continued)

FOREIGN PATENT DOCUMENTS

CN    104388307 A    3/2015
CN    105300943 A    2/2016
(Continued)

OTHER PUBLICATIONS

English Machine Translation of CN105784611A (Year: 2016).*

*Primary Examiner* — Dominic J Bologna
(74) *Attorney, Agent, or Firm* — Chiwin Law LLC (57) ABSTRACT

A detection apparatus and a detection method. The detection apparatus includes: a main body, a detection assembly, and a detection object receiving portion. The detection assembly includes: a signal transmitter, configured to transmit detection signals; a signal receiver, configured to receive at least part of the detection signals transmitted by the signal transmitter; and a detection connection portion, connected to the signal transmitter and the signal receiver and causing the signal transmitter and the signal receiver to be spaced from each other by the detection connection portion. The detec-
(Continued)

tion object receiving portion is configured to receive a detection object. The detection object receiving portion and the detection assembly are relatively movably arranged on the main body so as to allow the detection object received by the detection object receiving portion to be located in a transmission path of the detection signals between the signal transmitter and the signal receiver.

15 Claims, 3 Drawing Sheets

(51) Int. Cl.
    *B01L 9/00*     (2006.01)
    *G01N 21/01*     (2006.01)
    *G01N 21/27*     (2006.01)
    *G01N 21/78*     (2006.01)
    *G01N 33/00*     (2006.01)

(52) U.S. Cl.
    CPC ............ *G01N 21/27* (2013.01); *G01N 33/00* (2013.01); *B01L 3/502715* (2013.01); *B01L 9/527* (2013.01); *B01L 2200/143* (2013.01); *B01L 2300/0609* (2013.01); *B01L 2300/0654* (2013.01); *B01L 2300/0663* (2013.01); *B01L 2300/0681* (2013.01); *B01L 2300/1894* (2013.01); *G01N 2021/0106* (2013.01); *G01N 21/78* (2013.01); *G01N 2201/02* (2013.01); *G01N 2201/0633* (2013.01)

(58) Field of Classification Search
    CPC ....... G01N 2021/0106; G01N 2201/02; G01N 2201/0633; B01L 3/5027; B01L 3/505; B01L 3/502715; B01L 9/527; B01L 2200/143; B01L 2300/0609; B01L 2300/0654; B01L 2300/0663; B01L 2300/0681; B01L 2300/1894

See application file for complete search history.

(56) References Cited

U.S. PATENT DOCUMENTS

| | | | | |
|---|---|---|---|---|
| 2007/0109342 A1* | 5/2007 | Kato | .................... | B41J 2/17566 347/19 |
| 2012/0001089 A1* | 1/2012 | Laitinen | ................. | G01N 21/13 356/244 |
| 2012/0067723 A1* | 3/2012 | Rearick | ................... | B01L 3/502 422/68.1 |
| 2013/0196276 A1* | 8/2013 | Lee | ......................... | C12M 23/16 432/32 |
| 2014/0111572 A1* | 4/2014 | Jin | ......................... | B41J 25/001 347/14 |
| 2015/0346097 A1* | 12/2015 | Battrell | .............. | G01N 21/6428 702/19 |
| 2016/0370348 A1* | 12/2016 | Oellermann | ....... | G01N 33/4925 |

FOREIGN PATENT DOCUMENTS

| | | | |
|---|---|---|---|
| CN | 105784611 A | * | 7/2016 |
| CN | 107748138 A | | 3/2018 |
| CN | 108414446 A | | 8/2018 |
| CN | 109709040 A | | 5/2019 |
| CN | 110763641 A | | 2/2020 |
| CN | 211347917 U | | 8/2020 |
| KR | 20190080999 A | | 7/2019 |

* cited by examiner

DETECTION DEVICE AND DETECTION METHOD

CROSS REFERENCES TO RELATED APPLICATIONS

This application is a U.S. National Phase Entry of International Application No. PCT/CN2020/127470 filed on Nov. 9, 2020, designating the United States of America and claiming priority to Chinese Patent Application No. 201911201283.5, filed on Nov. 29, 2019. The present application claims priority to and the benefit of the above-identified applications and the above-identified applications are incorporated by reference herein in their entirety.

TECHNICAL FIELD

The embodiment of the present disclosure relates to a detection apparatus and a detection method.

BACKGROUND

Microfluidic technology integrates basic units of a whole process of analyzing samples in the fields of biology, chemistry, and medicine (sample extraction, reagent sample reaction, cleaning, detection) on a micron-scale chip, and completes the whole process of analysis by capillary action or active control.

Compared with the traditional biochemical detection, a microfluidic chip platform has advantages of small size, easy to carry, fast detection speed, being able to meet the requirements of emergency and realize multi-channel simultaneous detection.

SUMMARY

At least one embodiment of the present disclosure provides a detection apparatus, comprising: a main body; a detection component, the detection component comprises: a signal transmitter configured to transmit a detection signal; a signal receiver configured to receive at least a portion of the detection signal transmitted by the signal transmitter; and a detection connection part, the detection connection part connects the signal transmitter and the signal receiver, and the signal transmitter and the signal receiver are spaced apart from each other by the detection connection part; and a detection object receiving part configured to receive a detection object, the detection object receiving part and the detection component are relatively movable on the main body, to allow a detection object received by the detection object receiving part to be located in a transmission path of the detection signal between the signal transmitter and the signal receiver.

For example, in the detection apparatus of at least one embodiment of the present disclosure, the signal transmitter comprises a light-emitting device to transmit an optical signal as the detection signal.

For example, in the detection apparatus of at least one embodiment of the present disclosure, the signal transmitter further comprises an optical collimation component, and the optical collimation component is configured to collimate the optical signal into parallel light.

For example, in the detection apparatus of at least one embodiment of the present disclosure, the optical collimation component comprises a convex lens.

For example, in the detection apparatus of at least one embodiment of the present disclosure, the optical collimation component further comprises a connecting element, and the connecting element comprises a surface with threads, so that the convex lens can be threadedly connected to the detection connection part.

For example, in the detection apparatus of at least one embodiment of the present disclosure, the signal receiver comprises a photoelectric converter, and the photoelectric converter is configured to convert the received optical signal into a detection result signal, and to output the detection result signal.

For example, in the detection apparatus of at least one embodiment of the present disclosure, the photoelectric converter comprises a photodiode.

For example, in the detection apparatus of at least one embodiment of the present disclosure, the signal receiver further comprises a light filter element, the light filter element is arranged in the transmission path, and allows the optical signal with a given wavelength in the received optical signal to pass through, to illuminate the photoelectric converter.

For example, in the detection apparatus of at least one embodiment of the present disclosure, the detection component further comprises a radiator, the radiator is arranged on the detection connection part and is thermally coupled to the signal transmitter.

For example, in the detection apparatus of at least one embodiment of the present disclosure, the detection connection part is provided with a U-shaped structure or a C-shaped structure, the U-shaped structure or the C-shaped structure allows the detection object to be located in an opening of the U-shaped structure or an opening of the C-shaped structure, and the signal transmitter and the signal receiver are respectively fixed on opposite branches of the U-shaped structure, or opposite branches the C-shaped structure.

For example, the detection apparatus of at least one embodiment of the present disclosure further comprises a guide rail, fixed on the main body, the detection component is movably arranged on the guide rail; and a driver drivingly connected with the detection component to drive the detection component to move along the guide rail.

For example, in the detection apparatus of at least one embodiment of the present disclosure, the driver comprises: a motor with an output shaft; a lead screw, the lead screw is connected with the output shaft of the motor to rotate under the drive of the motor, and the lead screw is parallel to the guide rail; and a screw nut, the screw nut is threadedly engaged with the lead screw and is movably arranged on the lead screw, and the screw nut is connected with the detection component and can drive the detection component.

For example, the detection apparatus of at least one embodiment of the present disclosure further comprises a position sensor, and the position sensor is arranged on the main body and is configured to generate a position signal in a case that the detection component is detected.

For example, in the detection apparatus of at least one embodiment of the present disclosure, the position sensor is arranged at an end of the guide rail.

For example, in the detection apparatus of at least one embodiment of the present disclosure, the position sensor comprises a slot-type photoelectric switch; and the detection component further comprises a baffle, and the baffle can be received in the slot of the slot-type photoelectric switch.

At least one embodiment of the present disclosure also provides a detection method, applicable to the detection apparatus according to any embodiment of the present disclosure. The detection method comprises: providing the detection signal illuminating the detection object by the signal transmitter; and receiving the detection signal irradiating and passing through the detection object by the signal receiver.

BRIEF DESCRIPTION OF THE DRAWINGS

In order to clearly illustrate the technical solution of the embodiments of the present disclosure, the drawings of the embodiments will be briefly described. It is apparent that the described drawings are only related to some embodiments of the present disclosure and are not limitative of the present disclosure.

DETAILED DESCRIPTION

The technical solutions of the embodiments will be described in a clearly and fully understandable way in connection with the related drawings. It is apparent that the described embodiments are just a part but not all of the embodiments of the present disclosure. Based on the described embodiments herein, those skilled in the art can obtain, without any inventive work, other embodiment(s) which should be within the scope of the present disclosure.

Unless otherwise defined, all the technical and scientific terms used herein have the same meanings as commonly understood by one of ordinary skill in the art to which the present disclosure belongs. The terms, such as "first," "second," or the like, which are used in the present disclosure, are not intended to indicate any sequence, amount or importance, but for distinguishing various components. The terms, such as "comprise/comprising," "include/including," or the like are intended to specify that the elements or the objects stated before these terms encompass the elements or the objects and equivalents thereof listed after these terms, but not preclude other elements or objects. The terms, "on," "under," or the like are only used to indicate relative position relationship, and when the absolute position of the object which is described is changed, the relative position relationship may be changed accordingly.

In order to keep the following descriptions of the embodiments of the present disclosure clear and concise, detailed descriptions of known functions and known components are omitted in the present disclosure.

Biochemical detection is to generate colored substances through biochemical reactions, the colored substances have absorption effect on light with a specific wavelength, and a substance content in a biochemical test item is identified by detecting an absorbance of the light in a wavelength band corresponding to the specific wavelength. However, a diameter of a detection hole of a microfluidic chip is generally on a micrometer scale, thus, accurate alignment, no spatial crosstalk, and scanning in motion are required.

At least one embodiment of the present disclosure provides a detection apparatus, which has advantages of simple structure, accurate alignment, easy to operate and debug, and space saving.

Figure 1:
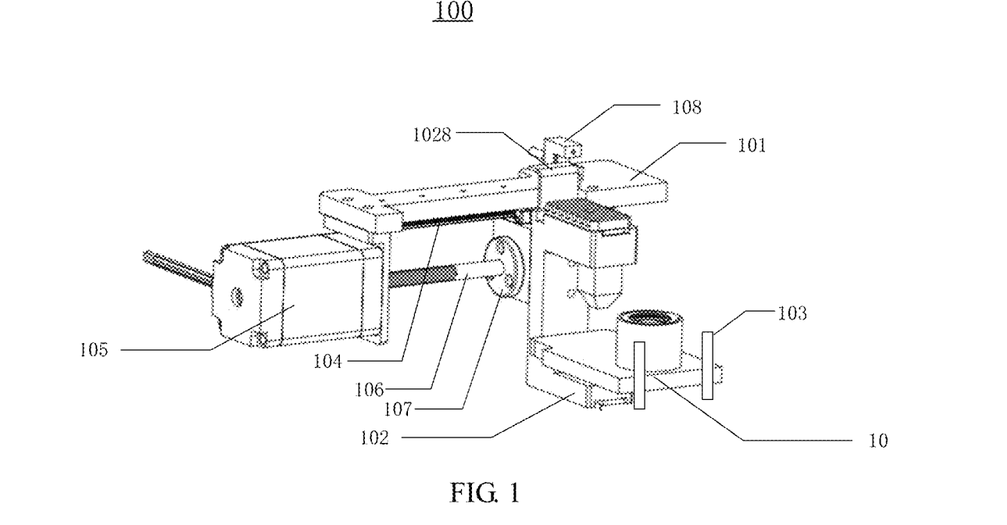
FIG. 1 is a schematically structural diagram of a detection apparatus according to at least one embodiment of the present disclosure, in which the detection component is located at a first position.
Figure 2:
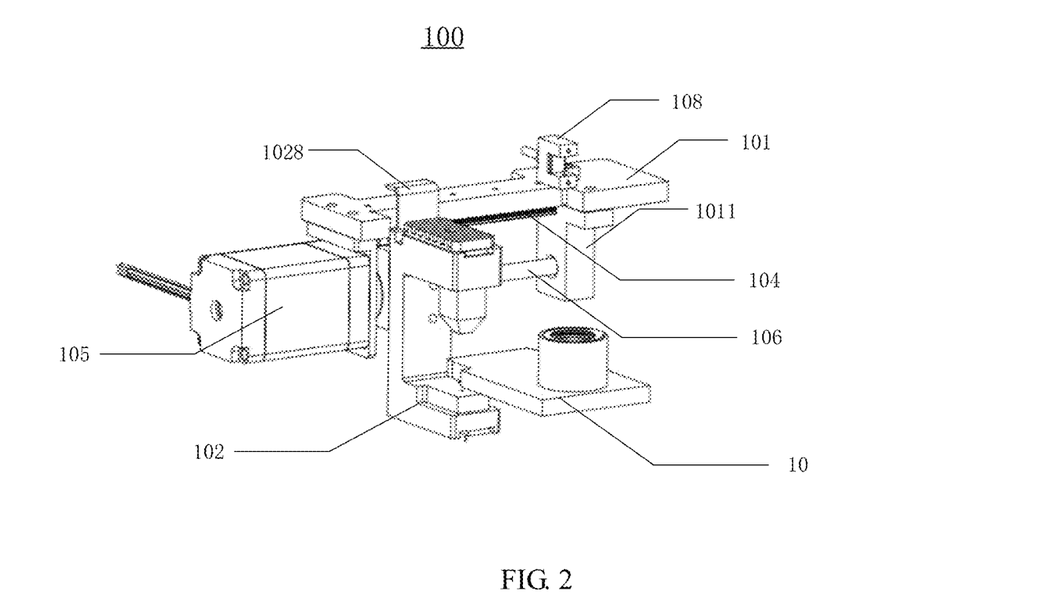
FIG. 2 is a schematically structural diagram of a detection apparatus according to at least one embodiment of the present disclosure, in which the detection component is located at a second position.
Figure 3:
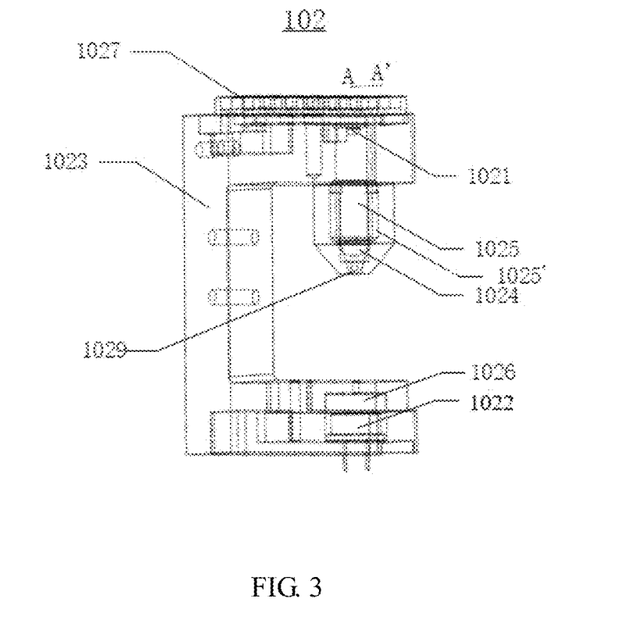
FIG. 3 is a perspective diagram of the structure of the detection component in the detection apparatus shown in FIGS. 1 and 2.
Figure 4:
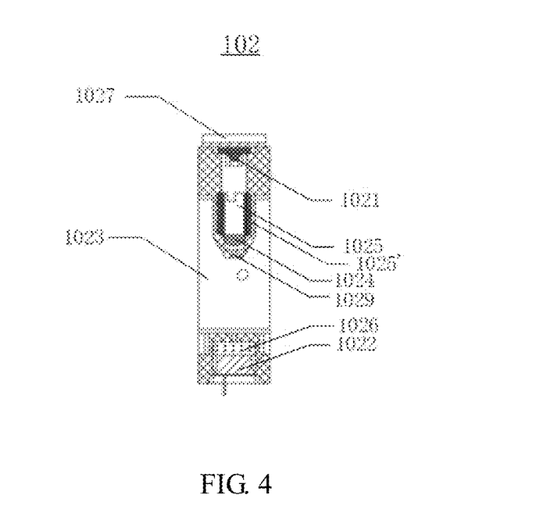
FIG. 4 is a side cross-sectional diagram taken along a line A-A' in FIG. 3.

FIG. 1 is a schematically structural diagram of a detection apparatus according to at least one embodiment of the present disclosure, in which the detection component is located at a first position. FIG. 2 is a schematically structural diagram of a detection apparatus according to at least one embodiment of the present disclosure, in which the detection component is located at a second position. FIG. 3 is a perspective schematic diagram of the structure of the detection component in the detection apparatus shown in FIGS. 1 and 2. FIG. 4 is a side cross-sectional diagram taken along a line A-A' in FIG. 3.

As shown in FIGS. 1 and 2, the detection apparatus 100 according to at least one embodiment of the present disclosure includes a main body 101, a detection component 102, and a detection object receiving part 103.

The detection component 102 is installed on the main body 101. It is to be understood that, in FIGS. 1 and 2, a plate-shaped main body 101 is only exemplary, the embodiments of the present disclosure are limited thereto. In other embodiments, the main body 101 can be in any suitable shapes, and can include any suitable structures, such as a base, a pillar, and so on.

The detection object receiving part 103 is used for receiving the detection object. In FIGS. 1 and 2, for ease of description, the detection object 10 is shown exemplarily, the detection object 10 may be, for example, a detection chip including a microfluidic chip, and the detection chip is provided with a detection part (such as a detection hole) to perform the above-mentioned biochemical detection. However, the embodiments of the present disclosure are not limited thereto, for example, the detection object 10 may also be other types, shapes, and structures.

In FIGS. 1 and 2, the detection object receiving part 103 exemplarily shows limit posts, the limit posts define a space for receiving a detection object, however, it is to be understood that, in other embodiments, the detection object receiving part 103 may further include a detection chip receiving structure for receiving the detection chip, such as a base, a holder, and so on, but the embodiments of the present disclosure are not limited thereto, for example, the detection object receiving part 103 in the embodiment of the present disclosure is configured to accommodate the detection object (that is, the detection chip).

The detection object receiving part 103 and the detection component 102 are relatively movable on the main body 101, which allows the detection object 10 received by the detection object receiving part 103 to be located in a transmission path of the detection signal between the signal transmitter and the signal receiver. For example, in some embodiments, the detection component 102 is movable, and the detection object receiving part 103 is fixed. For example, in some embodiments, the detection component 102 is fixed, and the detection object receiving part 103 is movable. For example, in some other embodiments, both the detection component 102 and the detection object receiving part 103 are movable. Hereinafter, as an example, the embodiments of the present disclosure will be described in which the detection component 102 is movable and the detection object receiving part 103 is fixed. By allowing the detection component 102 to move, and allowing the detection object receiving part 103 and the detection object 10 on the detection object receiving part 103 to be fixed, the fixing of the detection object 10 is facilitated, the accurate control of micro pumps and micro valves of the detection object 10 can be realized.

The detailed structure of the detection component according to at least one embodiment of the present disclosure will be described below in conjunction with FIG. 3 and FIG. 4. As shown in FIG. 3 and FIG. 4, the detection component 102 includes a signal transmitter, a signal receiver, and a detection connection part 1023.

The signal transmitter is configured to transmit a detection signal. The signal receiver is configured to receive at least a portion of the detection signal transmitted by the signal transmitter. The detection connection part 1023 connects the signal transmitter and the signal receiver, and the signal transmitter and the signal receiver are spaced apart from each other by the detection connection part 1023.

Because the signal transmitter and the signal receiver are connected and fixed by the detection connection part 1023, the positions of the signal transmitter and the position of the signal receiver are relatively motionless, so that a measurement error caused by a relative position error between the signal transmitter and the signal receiver is avoided, the assembly difficulty is reduced, and the detection accuracy is increased.

For example, the above-mentioned signal transmitter may include a light-emitting device 1021 to transmit an optical signal as a detection signal. For example, in some embodiments, the light-emitting device 1021 may include a light-emitting diode.

However, it is to be understood that the embodiments of the present disclosure are not limited thereto. For example, in some embodiments, the signal transmitter can emit acoustic waves, microwaves, X-rays, gamma rays, infrared rays, ultraviolet rays, etc.

For example, in some embodiments, the signal transmitter may further include an optical collimation component 1024. The optical collimation component 1024 is configured to collimate the optical signal emitted by the light-emitting device 1021 into parallel light. For example, the optical signal transmitted by the light-emitting device 1021 is collimated by the optical collimation component 1024, so that more optical signals are allowed to pass through an aperture 1029 of the detection component 102, and the utilization rate of the optical signal transmitted by the light-emitting device 1021 is improved. In some embodiments, the optical collimation component 1024 may include one or more convex lenses.

For example, in some embodiments, the optical collimation component 1024 may be connected to the detection connection part 1023. For example, the optical collimation component 1024 may also include a connecting element 1025, the connecting element 1025 includes a surface 1025' with threads, so that the optical collimation component 1024 (for example, the above-mentioned convex lens) can be threadedly connected to the detection connection part 1023.

However, it is to be understood that, in some embodiments, the signal transmitter of the detection component 102 may not include the optical collimation component 1024, so that the volume of the detection apparatus 100 is reduced, and the portability of the detection apparatus 100 is improved.

For example, in some embodiments, the above-mentioned signal receiver may include a photoelectric converter 1022. However, it is to be understood that, in a case that the signal transmitter transmits other types of detection signals, corresponding types of the signal receivers should also be used, to be able to receive and process the corresponding detection signals.

The photoelectric converter 1022 is configured to convert the received optical signal into an electrical signal, and to output the electrical signal. For example, the photoelectric converter 1022 can be connected to an analytical instrument, and can output the converted electrical signal to the analysis instrument, furthermore, by comparing an intensity of the emitted light of the light-emitting device 1021 with an intensity of the received light of the photoelectric converter 1022, an absorbance value of a sample in the detection object 10 can be obtained, and a substance content of the sample in the detection object 10 can be obtained. For example, the intensity of the emitted light of the above-mentioned light-emitting device 1021 can be obtained by placing a standard container or a standard article in the detection apparatus 100 for detecting.

For example, in some embodiments, the photoelectric converter 1022 may include a photodiode. For example, the photoelectric converter 1022 may include a silicon photovoltaic cell.

For example, the detection component 102 may include a plurality of light-emitting devices 1021 and a plurality of corresponding photoelectric converters 1022, the plurality of the light-emitting devices 1021 can emit different detection signals (for example, optical signals of different wavelengths), so that the detection apparatus 100 can be used to detect a variety of different samples, and the scope of application of the detection apparatus 100 is expanded.

For example, in some embodiments, the above-mentioned signal receiver may further include a light filter element 1026. The light filter element 1026 is arranged in the transmission path of the detection signal between the signal transmitter and the signal receiver, and the light filter element 1026 allows the optical signal with a given wavelength in the received optical signals to pass through, to illuminate the photoelectric converter 1022. Exemplarily, a center wavelength of the light filter element 1026 may be 550 nanometers. By arranging the light filter element 1026, stray light can be prevented from irradiating the photoelectric converter 1022, and only the optical signal with the given wavelength is allowed to irradiating the photoelectric converter 1022, so that the accuracy of detection can be improved.

For example, in some embodiments, the detection component 102 may further include a radiator 1027. The radiator 1027 is arranged on the detection connection part 1023 and is thermally coupled with the signal transmitter. For example, as shown in FIG. 3, the radiator 1027 is arranged on the detection connection portion 1023 and is thermally coupled to the signal transmitter, specifically, the radiator is thermally coupled to the light-emitting device 1021 in the signal transmitter. The radiator 1027 can conduct heat generated by the signal transmitter (for example, the light-emitting device 1021 of the signal transmitter) to the surrounding environment, so that it can avoid the signal transmitter from overheating and working improperly or even burning out.

As shown in FIG. 3, in some embodiments, the detection connection part 1023 may have a U-shaped structure, or a C-shaped structure. For example, the U-shaped structure allows the detection object 10 to be located in the opening of the U-shaped structure, and the signal transmitter (such as the light-emitting device 1021, the optical collimation component 1024, and the connecting element 1025) and the signal receiver (such as the photoelectric converter 1022 and the light filter element 1026) are respectively fixed on the opposite branches of the U-shaped structure. In some embodiments, the opening of the U-shaped structure and the relative position relationship of the U-shaped structure can be adjusted according to the shape of the detection object 10, to ensure that a detection part (e.g., a detection hole) of the detection object 10 is aligned with the center of the aperture 1029 of the detection component 102, but the embodiment of the present disclosure is not limited thereto.

It is to be understood that, in other embodiments, the detection connection part 1023 may be in other suitable shapes.

For example, the detection apparatus according to at least one embodiment of the present disclosure may further include a guide rail and a driver, for example, it may include one guide rail or two guide rails. The guide rail(s) is/are fixed on the main body, and the detection component is movably arranged on the guide rail(s). The guide rail(s) play(s) a restriction role, and the freedom degree of the detection component is restricted. The detection component is only allowed to move in a straight line, and not allowed to swing. For example, two guide rails can have a better stability effect. The driver is drivingly connected with the detection component to drive the detection component to move along the guide rail(s).

In FIGS. 1 and 2, it is exemplarily shown that the driver adopts a combination form of a rotating motor and a lead screw. The combination form of the rotating motor and the lead screw has advantages of precise movement, space saving, and low cost. However, it is to be understood that the embodiments of the present disclosure are not limited thereto. For example, in other embodiments, the driver can also be a linear motor, the linear motor is coupled with the detection component, so that the detection component is driven to move along the guide rail(s).

As shown in FIG. 1 and FIG. 2, the detection apparatus 100 includes a guide rail 104. The driver is implemented to include a motor 105, a lead screw 106, and a screw nut 107 (for example, a flange).

The motor 105 is a rotating electric motor, and has an output shaft. The lead screw 106 is coupled with the output shaft of the motor 105, so that the lead screw 106 is driven by the motor 105 to rotate. The lead screw 106 is parallel to the guide rail 104. The lead screw 106 can be connected between the motor 105 and a lead screw support part 1011, and the lead screw support part 1011 is fixed with respect to the lead screw 106 and the motor 105. The lead screw support part 1011 can be connected to the main body 101, or the lead screw support part 1011 may be a portion of the main body 101. For example, a bearing may be installed in the lead screw support part 1011, an inner ring of the bearing can rotate with the lead screw, so as to avoid the lead screw from bearing unfavorable torque, which may otherwise lead to the inaccurate movement positioning. However, the embodiment of the present disclosure is not limited thereto. By arranging the lead screw support part 1011, adverse torque can be avoided.

The screw nut 107 is threadedly engaged with the lead screw 106 and is movably arranged on the lead screw 106, and the screw nut 107 is connected to the detection component 102 and can drive the detection component 102. The screw nut 107 is arranged to be able to move on the lead screw 106 in a case that the lead screw 106 is driven to rotate by the motor 105. The screw nut 107 is slidably connected to the guide rail 104, the guide rail 104 acts as a constraint to the screw nut 107, so that the detection component 102 connected with the screw nut 107 can move along the guide rail 104. The screw nut 107 may be directly connected to the guide rail 104, or the screw nut 107 may be connected to the guide rail 104 by other elements (for example, the detection component 102), but the embodiment of the present disclosure is not limited thereto.

The detection component 102 may be detachably connected to the screw nut 107, or may be fixedly connected to the screw nut 107. The detection component 102 can be directly connected to the screw nut 107, or the detection component 102 is integrally formed with the screw nut 107, or the detection component 102 may be fixedly connected to the screw nut 107 by other elements, but the embodiment of the present disclosure is not limited to these.

For example, the detection apparatus according to at least one embodiment of the present disclosure may further include a position sensor. The position sensor is arranged on the main body and is configured to generate a position signal in a case that the detection component is detected, and the position signal is used to control a position or movement of the detection component.

As shown in FIGS. 1 and 2, the detection apparatus 100 further includes a position sensor 108. The position sensor 108 may be arranged on the main body 101 and is configured to generate a position signal in a case that the detection component 102 is detected. For example, the position sensor 108 is configured to generate a position signal for the motor 105 in a case that the detection component 102 is in the first position shown in FIG. 1. For example, the first position may correspond to an origin position of the motor 105, the position signal is used to reset the motor 105, and the position sensor 108 can send the position signal generated when the detection component 102 is in the first position to the controller that controls the motor 105, so that the motor 105 is reset under the control of the controller. By arranging the position sensor 108, the motor 105 can be origin reset, so that a precise positioning of the detection component 102 can be realized.

For example, the position sensor 108 can be arranged at an end of the guide rail 104, but it is to be understood that the embodiments of the present disclosure are not limited thereto. In other embodiments, the position sensor 108 may be arranged at any suitable positions according to actual requirements.

In the embodiment of the present disclosure, the detection component 102 is driven by the motor 105 to move along the guide rail 104. A length of a movement stroke of the detection component 102 can be determined according to actual requirements, for example, according to a width of a region of the detection object 10 to be detected in a moving direction of the detection component 102. In FIG. 1, the detection component 102 is at the first position, that is, at an end of the moving stroke of the detection component 102 away from the motor 105. In FIG. 2, the detection component 102 is at a second position, that is, at an end of the moving stroke of the detection component 102 near the motor 105. For example, the detection component 102 can perform a fixed-point detection or a motion scanning detection on the detection object 10, for example, a continuous scanning detection, but the embodiments of the present disclosure are not limited thereto.

In some embodiments, the position sensor 108 may include a transmitting part for transmitting a position detection signal and a receiving part for receiving the position detection signal emitted by the transmitting part, and the position sensor 108 can generate an indication signal in a case that the receiving part does not receive the position detection signal emitted by the transmitting part; and in this case, the detection component 102 may also include a baffle 1028, which can be fixedly connected with the detection component 102 to move synchronously with the detection component 102, and the baffle 1028 is arranged to be located between the transmitting part and the receiving part of the position sensor 108 in a case that the detecting component 102 is in the first position, so that the receiving part of the position sensor 108 cannot receive the detection signal emitted by the transmitting part, and the position sensor 108 generates a position signal. However, it is to be understood that, for example, the baffle 1028 may also be fixedly connected to at least one of the screw nut 107 or the detection component 102, but the embodiment of the present disclosure is not limited thereto.

For example, the position sensor 108 may include a groove-type photoelectric switch, the baffle 1028 is configured to be received in the groove of the groove-type photoelectric switch, and in a case that the baffle 1028 is received in the groove of the groove-type photoelectric switch, the baffle 1028 can prevent the signal emitted by a signal transmitting end of the groove-type photoelectric switch from reaching the signal receiving end of the groove-type photoelectric switch. The baffle 1028 can be made of any suitable material, such as metal, wood, and plastic, but the embodiments of the present disclosure are not limited thereto, and the baffle 1028 can prevent the signal emitted from the signal transmitting end of the groove-type photoelectric switch from reaching the signal receiving end of the groove-type photoelectric switch. For example, in other embodiments, the position sensor 108 may also be a proximity sensor arranged at the first position, in a case that the position sensor 108 detects that a distance away from a detection component 102 is less than a preset value, it is determined that the detection component 102 is at the first position.

Figure 5:
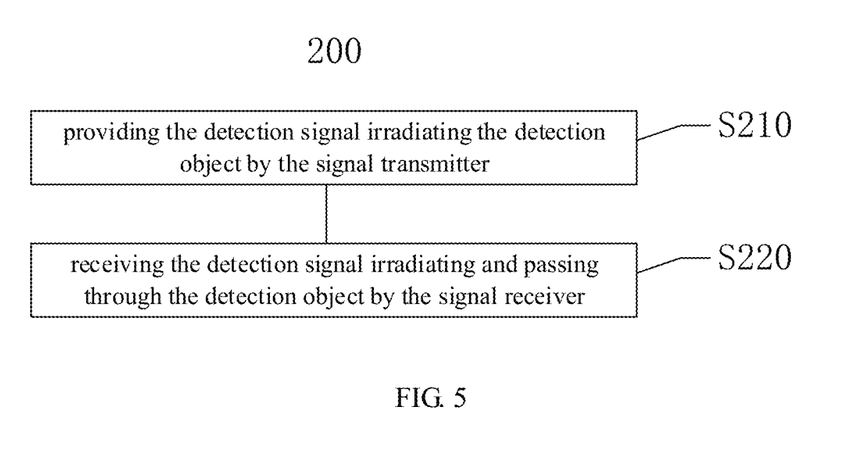
FIG. 5 is a flowchart of a detection method according to at least one embodiment of the present disclosure.

At least one embodiment of the present disclosure also provides a detection method applicable to the detection apparatus of any embodiment of the present disclosure. FIG. 5 is a flowchart of a detection method according to at least one embodiment of the present disclosure. As shown in FIG. 5, the detection method 200 according to at least one embodiment of the present disclosure includes following steps.

S210: providing the detection signal illuminating the detection object by the signal transmitter; and S220: receiving the detection signal irradiating and passing through the detection object by the signal receiver.

The following points should be noted:

(1) The drawings of the embodiments of the present disclosure only relate to the structures related to the embodiments of the present disclosure, and other structures can refer to common designs.

(2) For the sake of clarity, in the drawings used to describe the embodiments of the present disclosure, the thickness and size of elements or components are enlarged. It is to be understood that in a case that a structure, such as an element or a component, is referred to as being "on" or "under" another structure, the structure may be "directly" "on" or "under" another element, or there may be intermediate element(s).

(3) Without conflict with each other, elements in a same embodiment or different embodiments of the present disclosure can be combined.

The description above is only about the embodiments of the present disclosure, and the scope of the present disclosure is not limited thereto. Any changes or substitutions readily conceived by an ordinary skill in the art within the technical scope of the embodiments of the present disclosure shall fall within the scope of the present disclosure.

What is claimed is:

1. A detection apparatus, comprising:
   a main body;
   a detection component, wherein the detection component comprises:
      a signal transmitter configured to transmit a detection signal;
      a signal receiver configured to receive at least a portion of the detection signal transmitted by the signal transmitter; and
      a connection part including a U-shaped structure or a C-shaped structure, wherein the U-shaped structure or the C-shaped structure allows a detection object to be located in an opening of the U-shaped structure or an opening of the C-shaped structure, wherein the connection part connects the signal transmitter and the signal receiver, and the signal transmitter and the signal receiver are spaced apart from each other by the connection part, and the signal transmitter and the signal receiver are respectively fixed on opposite branches of the U-shaped structure, or opposite branches of the C-shaped structure;
   a detection object receiving part including limit posts configured to receive a detection object, wherein the detection object receiving part and the detection component are relatively movable on the main body transversely along the arrangement of a guide rail of the detection component, to allow a detection object received by the detection object receiving part to be located in a transmission path of the detection signal between the signal transmitter and the signal receiver, and the guide rail is fixed on the main body, wherein the detection component is movably arranged on the guide rail; and
   a driver drivingly connected with the detection component to drive the detection component to move along the guide rail; wherein the driver comprises:
      a motor with an output shaft;
      a lead screw, wherein the lead screw is connected with the output shaft of the motor to rotate under the drive of the motor, and the lead screw is parallel to the guide rail; and
      a screw nut, wherein the screw nut is threadedly engaged with the lead screw and is movably arranged on the lead screw, and the screw nut is connected with the detection component and drives the detection component to move along the guide rail.

2. The detection apparatus according to claim 1, wherein the signal transmitter comprises a light-emitting device to transmit an optical signal as the detection signal.

3. The detection apparatus according to claim 2, wherein the signal receiver comprises a photoelectric converter, and the photoelectric converter is configured to convert the received optical signal into an electrical signal, and to output the electrical signal.

4. The detection apparatus according to claim 3, wherein the photoelectric converter comprises a photodiode.

5. The detection apparatus according to claim 3, wherein the signal receiver further comprises a light filter element, the light filter element is arranged in the transmission path, and allows the optical signal with a given wavelength in the received optical signal to pass through, to illuminate the photoelectric converter.

6. The detection apparatus according to claim 2, wherein the signal transmitter further comprises an optical collimation component, the optical collimation component comprises a convex lens and is configured to collimate the optical signal into parallel light.

7. The detection apparatus according to claim 6, wherein the optical collimation component further comprises a connecting element, and the connecting element comprises a surface with threads, so that the convex lens can be threadedly connected to the connection part.

8. The detection apparatus according to claim 7, wherein the signal receiver comprises a photoelectric converter, the photoelectric converter is configured to convert the received optical signal into an electrical signal, and to output the electrical signal.

9. The detection apparatus according to claim 1, wherein the signal transmitter further comprises an optical collimation component, and the optical collimation component comprises a convex lens and is configured to collimate the optical signal into parallel light.

10. The detection apparatus according to claim 9, wherein the optical collimation component further comprises a connecting element, and the connecting element comprises a surface with threads, so that the convex lens can be threadedly connected to the connection part.

11. The detection apparatus according to claim 1, wherein the detection component further comprises a radiator, wherein the radiator is arranged on the connection part and is thermally coupled to the signal transmitter.

12. The detection apparatus according to claim 1, further comprising: a position sensor, wherein the position sensor is arranged on the main body and is configured to generate a position signal in a case that the detection component is detected.

13. The detection apparatus according to claim 12, wherein the position sensor comprises a slot-type photoelectric switch; and
the detection component further comprises a baffle, and the baffle can be received in the slot of the slot-type photoelectric switch.

14. The detection apparatus according to claim 1, further comprising: a position sensor, wherein the position sensor is arranged at an end of the guide rail.

15. A detection method, applicable to the detection apparatus according to claim 1, wherein the detection method comprises:
providing the detection signal illuminating the detection object by the signal transmitter; and
receiving the detection signal irradiating and passing through the detection object by the signal receiver.

* * * * *